US009456600B2

(12) United States Patent
Inoue et al.

(10) Patent No.: US 9,456,600 B2
(45) Date of Patent: Oct. 4, 2016

(54) AGRICULTURAL CHEMICAL-SPREADING AGENT COMPOSITION

(75) Inventors: Masaki Inoue, Wakayama (JP); Masatoshi Kamei, Wakayama (JP)

(73) Assignee: Kao Corporation, Tokyo (JP)

( * ) Notice: Subject to any disclaimer, the term of this patent is extended or adjusted under 35 U.S.C. 154(b) by 27 days.

(21) Appl. No.: 13/820,357

(22) PCT Filed: Sep. 1, 2011

(86) PCT No.: PCT/JP2011/069864
§ 371 (c)(1),
(2), (4) Date: Mar. 18, 2013

(87) PCT Pub. No.: WO2012/029894
PCT Pub. Date: Mar. 8, 2012

(65) Prior Publication Data
US 2013/0203599 A1    Aug. 8, 2013

(30) Foreign Application Priority Data

Sep. 3, 2010    (JP) .................................. 2010-197726
Aug. 11, 2011   (JP) .................................. 2011-175791

(51) Int. Cl.
*A01N 25/30*    (2006.01)
*A01N 25/04*    (2006.01)
*A01N 25/24*    (2006.01)

(52) U.S. Cl.
CPC .............. *A01N 25/30* (2013.01); *A01N 25/04* (2013.01); *A01N 25/24* (2013.01)

(58) Field of Classification Search
CPC ...... A01N 25/04; A01N 25/30; A01N 25/24; A01N 47/38; A01N 57/14
USPC .......................... 504/206; 514/369, 395, 132
See application file for complete search history.

(56) References Cited

U.S. PATENT DOCUMENTS

| | | | |
|---|---|---|---|
| 2001/0031703 A1* | 10/2001 | Ueda ............................ | 504/127 |
| 2002/0107147 A1 | 8/2002 | Hayashi et al. | |
| 2003/0125212 A1 | 7/2003 | Yamaguchi et al. | |
| 2003/0216261 A1 | 11/2003 | Hayashi et al. | |
| 2005/0261133 A1 | 11/2005 | Nakanishi et al. | |
| 2010/0234436 A1 | 9/2010 | Dairiki et al. | |

FOREIGN PATENT DOCUMENTS

| | | | |
|---|---|---|---|
| CN | 101361477 A | 2/2009 | |
| CN | 101380002 A | 3/2009 | |
| JP | 6-329503 A | 11/1994 | |
| JP | 9-77617 A | 3/1997 | |
| JP | 9-110617 A | 4/1997 | |
| JP | 9-278605 A | 10/1997 | |
| JP | 10-231202 A | 9/1998 | |
| JP | 11-71202 A | 3/1999 | |
| JP | 11-147803 A | 6/1999 | |
| JP | 11-349403 A | 12/1999 | |
| JP | 2000-1404 A | 1/2000 | |
| JP | 2000-198703 A | 7/2000 | |
| JP | 2001-288006 A | 10/2001 | |
| JP | 2003-300801 A | 10/2003 | |
| JP | 2005-132741 A | 5/2005 | |
| JP | 2005-330221 A | 12/2005 | |
| JP | 2005-344076 A | 12/2005 | |
| JP | 2006-137728 A | 6/2006 | |
| JP | 2007-169217 A | 7/2007 | |
| JP | 2007-176855 A | 7/2007 | |
| JP | 2009-522332 A | 6/2009 | |
| JP | 2012-72110 A | 4/2012 | |
| WO | WO 2007/077246 A2 | 7/2007 | |
| WO | WO 2008/032671 A1 | 3/2008 | |
| WO | WO 2012/029893 A1 | 3/2012 | |

OTHER PUBLICATIONS

Klis et al.; Title: Effect of a soluble polysaccharide (carboxy methyl cellulose) on the physico-chemical conditions in the gastrointestinal tract of broilers; Br Poult Sci.; vol. 34(5), pp. 971-983, Dec. 1993.*
International Search Report, issued in PCT/JP2011/069864, dated Nov. 1, 2011.
Chinese Office Action and Search Report for Chinese Application No. 201180052214.8, dated Feb. 21, 2014, with a partial English translation.
International Preliminary Report on Patentability (dated Apr. 9, 2013) and the English translation of the Written Opinion of the International Searching Authority (dated Nov. 1, 2011) for Application No. PCT/JP2011/069864 (Forms PCT/IB/373 and PCT/ISA/237).
Japanese Decision for Grant dated Oct. 13, 2015 for Application No. 2011-175791.

* cited by examiner

*Primary Examiner* — Johann R Richter
*Assistant Examiner* — Yanzhi Zhang
(74) *Attorney, Agent, or Firm* — Birch, Stewart, Kolasch & Birch, LLP

(57) ABSTRACT

The present invention provides the agricultural chemical-spreading agent composition, containing: (A) a polysaccharide in an amount of 5 to 30% by weight; (B) a polyoxyalkylene sorbitan fatty acid ester in an amount of 5 to 40% by weight; and (C) at least one nonionic surfactant selected from polyoxyalkylene alkyl ethers, sorbitan fatty acid esters, and silicone surfactants in an amount of 5 to 40% by weight, wherein the component (A) has a viscosity of not less than 5000 mPa·s in the form of a 5% by weight aqueous solution at 25° C., and a weight ratio of contents of the component (A) to the sum of components (B) and (C), (A)/[(B)+(C)], is 10/90 to 40/60.

14 Claims, No Drawings

AGRICULTURAL CHEMICAL-SPREADING AGENT COMPOSITION

FIELD OF THE INVENTION

The present invention relates to an agricultural chemical-spreading agent composition and an agricultural chemical composition.

BACKGROUND OF THE INVENTION

Agricultural chemicals such as pesticides, bactericides, plant growth hormones, and herbicides can exert their effects only by being absorbed into a body of a plant, an animal such as an insect, or the like. However, both plants and insects often have a water-repellant property to reject an aqueous agricultural chemical solution such that plants have a wax lipoid-secreting, a fuzzy surface, or a finely irregular surface, and insects have a layer similar to a keratin layer on the surface. Agricultural chemicals thus face the problem of failing to achieve desired effects when applied.

For the purpose of covering the problem, agricultural chemical-spreading agents have been widely used in the field of agriculture, particularly in emulsions and wettable powders of agricultural chemicals, to improve wetting and spreading performances thereof. The agricultural chemical-spreading agent contains a surfactant as a principal ingredient and reduces the surface tension of an agricultural chemical composition with the surfactant to improve wetting and spreading performances of the composition, and in practical use, further influences physical properties of the composition such as of emulsifying, dispersing, penetrating, fixing, suspending, and defoaming. The spreading agent for an agricultural chemical is thus an important adjuvant.

Examples of the agricultural chemical-spreading agent having been conventionally known include nonionic surfactants such as polyoxyethylene sorbitan esters, polyoxyethylene alkyl (or aryl)ethers, and polyoxyethylene fatty acid esters; anionic surfactants such as linear alkylbenzenesulfonates, dialkylsulfosuccinates, lignin sulfonates, and polynaphthyl sulfonates; and polymers such as polyacrylates.

For example, JP-A06-329503, JP-A09-278605, and JP-A10-231202 describe use of a specific nonionic surfactant produced by adding an alkylene oxide in an agricultural chemical-spreading agent. JP-A2000-001404 discloses an agricultural chemical-spreading agent composition containing a sorbitan fatty acid ester, a polyoxyethylene alkyl ether, and a polyether-modified silicone at specific proportions. JP-A2001-288006 discloses an agricultural chemical-spreading agent composition containing two surfactants having different melting points and describes that the spreading agent composition has a good stability at low temperature. JP-A2007-176855 discloses an agricultural chemical-spreading agent composition containing a cationic compound and an anionic oligomer or polymer, in which an anionic residue of an acid group serves as a counter ion of the cationic compound. Furthermore, JP-A2005-132741 proposed a water-dispersible granule for agriculture and horticulture, containing a cellulose derivative having a viscosity of 10 to 2000 mPa·s in the form of 2% by weight aqueous solution as a fixing agent in order to prevent an agricultural chemical from running off from a leaf or the like due to rainfall or the like.

JP-A09-077617 discloses use of a milbemycin compound to promote effects of an active ingredient, thereby preventing pines from dying. JP-A09-110617 discloses use of tebufenpyrad to promote effects of an active ingredient, thereby preventing pines from dying. JP-A11-147803 discloses use of pyrimidifen to promote effects of an active ingredient, thereby preventing pines from dying. JP-A11-071202 discloses a bactericide composition containing a bactericide and soluble starch. JP-B2009-522332 discloses a liquid concentrate containing a difficulty soluble, organic agricultural chemical compound and a solvent mixture. WO-A2008/032671 discloses a pest control agent in a suspension form, containing a cationic pest control active ingredient or an acid, a nonionic thickener, a nonionic surfactant, a solid active ingredient, and water.

SUMMARY OF THE INVENTION

The present invention relates to an agricultural chemical-spreading agent composition, containing: (A) a polysaccharide [hereinafter, referred to as component (A)] in an amount of 5 to 30% by weight; (B) a polyoxyalkylene sorbitan fatty acid ester [hereinafter, referred to as component (B)] in an amount of 5 to 40% by weight; and (C) at least one nonionic surfactant selected from polyoxyalkylene alkyl ethers, sorbitan fatty acid esters, and silicone surfactants [hereinafter, referred to as component (C)] in an amount of 5 to 40% by weight, wherein the component (A) has a viscosity of not less than 5000 mPa·s in the form of a 5% by weight aqueous solution at 25° C., and a weight ratio of contents of the component (A) to the sum of components (B) and (C), (A)/[(B)+(C)], is 10/90 to 40/60.

The present invention also relates to an agricultural chemical composition containing the agricultural chemical-spreading agent composition of the present invention and an agricultural chemical ingredient selected from active ingredients in bactericides, pesticides, miticides, herbicides, and plant growth regulators.

The present invention also relates to a method for producing an agricultural product, containing a step of applying the agricultural chemical-spreading agent composition of the present invention and an agricultural chemical ingredient selected from active ingredients in bactericides, pesticides, miticides, herbicides, and plant growth regulators to a subject sensitive to the agricultural chemical ingredient.

The present invention also relates to a method for producing an agricultural product, containing a step of applying the agricultural chemical composition of the present invention to a subject sensitive to the agricultural chemical ingredient.

The present invention also relates to a method for efficacy-enhancing an agricultural chemical by applying the agricultural chemical ingredient, selected from active ingredients in bactericides, pesticides, miticides, herbicides, and plant growth regulators, together with the agricultural chemical-spreading agent composition of the present invention to a subject sensitive to the agricultural chemical ingredient. The present invention further relates to use of the agricultural chemical-spreading agent composition of the present invention for efficacy-enhancing an agricultural chemical ingredient selected from active ingredients in bactericides, pesticides, miticides, herbicides and plant growth regulators.

DETAILED DESCRIPTION OF THE INVENTION

Conventional agricultural chemical-spreading agents composition can improve wetting and spreading performances of agricultural chemicals, but cannot fully prevent them from running down. Although JP-A2005-132741 discloses a technique for preventing an agricultural chemical from running down from a leaf or the like, its effects are not enough.

The present invention provides an agricultural chemical-spreading agent composition, that can improve wetting and spreading performances of an agricultural chemical, and prevent the agricultural chemical from running down from an applied subject such as a plant and an insect to increase an attached amount, thereby significantly efficacy-enhancing an agricultural chemical, and that is easily prepared and has good storage stability.

According to the agricultural chemical-spreading agent composition and the agricultural chemical composition of the present invention, an agricultural chemical has improved wetting and spreading performances and a drop of the agricultural chemical hardly runs down from an applied subject such as a plant and an insect to increase an attached amount, thereby significantly efficacy-enhancing an agricultural chemical. According to the method for producing an agricultural product of the present invention, attachment of an agricultural chemical ingredient to a subject is improved, resulting in increased productivity. The agricultural chemical-spreading agent composition of the present invention can be easily prepared in the form of a single liquid composition, and has good storage stability.

The agricultural chemical-spreading agent composition of the present invention contains (A) a polysaccharide [component (A)] in an amount of 5 to 30% by weight; (B) a polyoxyalkylene sorbitan fatty acid ester [component (B)] in an amount of 5 to 40% by weight; and (C) at least one nonionic surfactant selected from polyoxyalkylene alkyl ethers, sorbitan fatty acid esters, and silicone surfactants [component (C)] in an amount of 5 to 40% by weight, wherein the component (A) has a viscosity of not less than 5000 mPa·s in the form of 5% by weight aqueous solution at 25° C., and a weight ratio of contents of the component (A) to the sum of components (B) and (C), (A)/[(B)+(C)], is 10/90 to 40/60.

It is not evident why the agricultural chemical-spreading agent composition of the present invention efficacy-enhances, but assumed that the component (A) having a high concentration increases a viscosity of a liquid drop. Further components (B) and (C) reduce the surface tension of the drop. Adequate proportions of the components (A) to (C) provide the drop with a good balance between the wetting and spreading performances and the viscosity and then good wetting and spreading performances and then prevent the agricultural chemical from running down, thereby significantly efficacy-enhancing of the agricultural chemical.

<Component (A)>

The component (A) used in the present invention is a polysaccharide. For preventing an agricultural chemical from running down, specific examples of the component (A) include guar gum, xanthane gum, starches, celluloses, tara gum, locust bean gum, carrageenan, and derivatives thereof. Examples of the guar gum derivative include hydroxypropyl guar gum, carboxymethyl hydroxypropyl guar gum, and cationic guar gum. Examples of the xanthane gum derivative include hydroxypropyl xanthane gum. Examples of the starch derivative include carboxymethylated starches, hydroxyalkylated starches, hydroxypropyl distarch, grafted starch, and starch acetate. Examples of the cellulose derivative include hydroxyethyl cellulose, hydroxypropyl cellulose, hydroxypropylmethyl cellulose, and carboxymethyl cellulose. Among these polysaccharides, for preventing an agricultural chemical from running down from a subject such as a plant and an insect to increase an amount of the agricultural chemical attached, preferably used is at least one polysaccharide selected from guar gum, xanthane gum, locust bean gum, starches, celluloses, and derivatives thereof, more preferably selected from guar gum, starches, celluloses and derivatives thereof, even more preferably selected from guar gum, guar gum derivatives, carboxymethylated starches, hydroxyalkylated starches, starch acetate, hydroxypropyl cellulose, and hydroxypropylmethyl cellulose, still even more preferably selected from guar gum, guar gum derivatives, and hydroxyalkylated starches, and yet still even more preferably selected from guar gum and guar gum derivatives.

For preventing a drop from running down and enhancing attachment of an active ingredient to a subject such as a plant and an insect, the component (A) in the present invention preferably has a viscosity in the form of 5% by weight aqueous solution (hereinafter, simply referred to as "5% viscosity") at 25° C. of not less than 5000 mPa·s, preferably not less than 10000 mPa·s, and more preferably not less than 50000 mPa·s. For increasing wetting and spreading performances, facilitation of preparation (that is, an easy preparation of a single-liquid composition, applied hereinafter), and improving storage stability, the 5% viscosity is preferably not more than 3500000 mPa·s, more preferably not more than 2500000 mPa·s, and even more preferably not more than 1000000 mPa·s. Collecting them together, the 5% viscosity is preferably 5000 to 3500000 mPa·s, more preferably 10000 to 3500000 mPa·s, even more preferably 50000 to 2500000 mPa·s, and still even more preferably 50000 to 1000000 mPa·s. Note that, the 5% viscosity is measured by the method described in Examples.

Note that, the component (A) used in the present invention may be a commercial product. Examples of the commercial product include Meypro series guar gums, available from Sansho Co., Ltd., starches of Kiprogum series and Piostarch series, available from Nippon Starch Chemical Co., Ltd., V is top series xanthane gums available from San-Ei Gen F.F.I., Inc., and HPC series celluloses available from Nippon Soda Co., Ltd., Metolose series celluloses available from Shin-Etsu Chemical Co., Ltd., and Klucel series celluloses available from Sansho Co., Ltd.

<Component (B)>

The component (B) used in the present invention is a polyoxyalkylene sorbitan fatty acid ester, and serves as an improving agent for wetting and spreading performances and attachment. For improving wetting and spreading performances and attachment, the polyoxyalkylene sorbitan fatty acid ester preferably has a polyoxyethylene group as a part of the polyoxyalkylene group composing a hydrophilic moiety. From the similar viewpoints, an average number of oxyalkylene groups is preferably 1 to 50, more preferably 6 to 40, and even more preferably 6 to 30. In the polyoxyalkylene sorbitan fatty acid ester, a hydrophobic moiety is preferably an alkyl group. The alkyl group may be linear or branched. For improving attachment, the alkyl group preferably has 8 to 22 carbon atoms, more preferably 10 to 18 carbon atoms, and even more preferably 12 to 18 carbon atoms. For improving stability, wetting and spreading performances, and attachment, the component (B) is preferably selected from polyoxyethylene (average number of ethyleneoxy groups: 6 to 30) sorbitan fatty acid (8 to 22 carbon atoms) esters, and particularly from polyoxyethylene sorbitan oleic acid esters, polyoxyethylene sorbitan lauric acid esters, and polyoxyethylene sorbitan palmitic acid esters.

<Component (C)>

The component (C) used in the present invention is at least one nonionic surfactant selected from polyoxyalkylene alkyl ethers, sorbitan fatty acid esters, and silicone surfactants. It makes the component (A) be thickened easier and improves storage stability of a composition, and serves as an improving agent for attachment of an agricultural chemical to a subject such as a plant and an insect. For facilitation of preparation and improving storage stability and attachment, the component (C) is preferably selected from sorbitan fatty acid esters.

For improving attachment of an agricultural chemical to a subject such as a plant and an insect, the polyoxyalkylene alkyl ether preferably has a polyoxyethylene group as a part of the polyoxyalkylene group composing a hydrophilic moiety. From the similar viewpoints, an average number of oxyalkylene groups is preferably 4 to 40, more preferably 6 to 20, and even more preferably 6 to 15. In the polyoxyalkylene alkyl ether, a hydrophobic moiety is preferably an alkyl group. The alkyl group may be linear or branched. For improving attachment of an agricultural chemical to a subject such as a plant and an insect, the alkyl group preferably has 8 to 22 carbon atoms, more preferably 10 to 18 carbon atoms, and even more preferably 12 to 18 carbon atoms.

In the sorbitan fatty acid ester, a hydrophobic moiety is preferably an alkyl group. The alkyl group may be linear or branched. For improving attachment of an agricultural chemical to a subject such as a plant and an insect, the alkyl group preferably has 8 to 22 carbon atoms, more preferably 10 to 18 carbon atoms, and even more preferably 12 to 18 carbon atoms.

Examples of the silicone surfactant include side chain-modified silicones [represented by the formula (1)], both ends-modified silicones [represented by the formula (2)], one end-modified silicones [represented by the formula (3)], and both ends- and side chain-modified silicones [represented by the formula (4)], and variations thereof having various hydrophilic substituents (variation of X in each formula), including polyether type silicones [represented by the formula (5)], polyglycerol type silicones [represented by the formula (6)], pyrrolidone type silicones [represented by the formula (7)], betaine type silicones [represented by the formula (8)], sulfate type silicones [represented by the formula (9)], phosphate type silicones [represented by the formula (10)], and quaternary salt type silicones [represented by the formula (11)]. Among these silicone surfactants, for facilitation of preparation and improving storage stability and attachment of an agricultural chemical to a subject such as a plant and an insect, preferred are polyether-modified silicone surfactant classified in polyether type silicones [represented by the formula (5)], and more preferred are polyoxyalkylene-modified heptamethyltrisiloxanes.

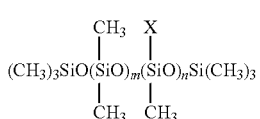

side chain-modified

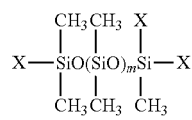

both ends-modified

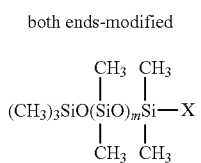

one end-modified

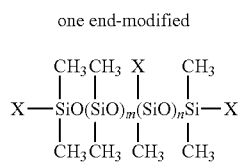

both ends- and side chain-modified wherein, m and n each represent the number of 0 to 100; and X represents a group selected from the following formulae (5) to (11), and preferably the formula (5):

polyether group

polyglycerin group

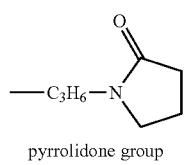

pyrrolidone group

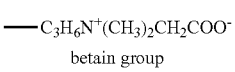

betain group

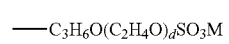

sulfate group

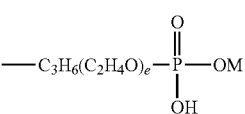

phosphate group

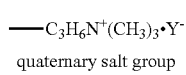

quaternary salt group wherein, a to e each represent an average number of groups added, ranging from 0 to 50; R represents a hydrocarbon group (and preferably an alkyl group) having 1 to 24 carbon atoms; M represents an alkaline metal such as sodium and potassium; and $Y^-$ represents a halide ion such as chloride.

<Component (D)>

The agricultural chemical-spreading agent composition of the present invention is preferably a liquid composition. In this case, an appropriate solvent or dispersing medium is used. Examples of the solvent or dispersing medium include water and organic solvents. For thickening the component (A), facilitation of preparation, and improving storage stability, the agricultural chemical-spreading agent composition of the present invention preferably contains an organic solvent, and more preferably (D) at least one organic solvent selected from polyhydric alcoholic solvents and glycol ether solvents [hereinafter, referred to as component (D)].

Examples of the polyhydric alcoholic solvent include lower polyhydric alcohols such as ethylene glycol, diethylene glycol, propylene glycol, dipropylene glycol, glycerol, diglycerol, and triglycerol. For thickening the component (A), facilitation of preparation, and improving storage stability, preferred are propylene glycol and diethylene glycol.

Examples of the glycol ether solvent include methyl cellosolve, ethyl cellosolve, ethylene glycol isopropyl ether, diethylene glycol monomethyl ether, triethylene glycol monomethyl ether, diethylene glycol dimethyl ether, and butyl cellosolve. For thickening the component (A), facilitation of preparation, and improving storage stability, preferred are diethylene glycol monomethyl ether and butyl cellosolve.

The component (D) is thus preferably at least one organic solvent selected from ethylene glycol, diethylene glycol, propylene glycol, diethylene glycol monomethyl ether, and butyl cellosolve.

<Compositional Characteristics of the Agricultural Chemical-Spreading Agent Composition>

For preventing a drop from running down from a subject such as a plant or an insect to increase an amount attached and efficacy-enhance an agricultural chemical, facilitation of preparation, improving storage stability of a composition, the agricultural chemical-spreading agent composition of the present invention contains the component (A) in an amount of 5 to 30% by weight, preferably 9 to 30% by weight, more preferably 10 to 25% by weight, and even more preferably 10 to 20% by For improving wetting and spreading performances of an agricultural chemical, thickening the component (A), and preventing a drop from running down from a subject such as a plant or an insect to increase an amount attached, thereby efficacy-enhancing the agricultural chemical, the agricultural chemical-spreading agent composition of the present invention contains the component (B) in an amount of 5 to 40% by weight, preferably 9 to 30% by weight, and more preferably 15 to 25% by weight.

For facilitation of preparation, thickening the component (A), and preventing a drop from running down from a subject such as a plant or an insect to increase an amount attached, thereby efficacy-enhancing an agricultural chemical, the agricultural chemical-spreading agent composition of the present invention contains the component (C) in an amount of 5 to 40% by weight, preferably 10 to 30% by weight, and more preferably 15 to 30% by weight.

For facilitation of preparation, improving storage stability of a composition, and thickening the component (A), the agricultural chemical-spreading agent composition of the present invention preferably contains the component (D) in an amount of 5 to 30% by weight, more preferably 10 to 30% by weight, and even more preferably 15 to 25% by weight. Among the solvent or dispersing medium, water may constitute the rest of the agricultural chemical-spreading agent composition of the present invention.

For facilitation of preparation, improving storage stability of a composition, thickening the component (A), improving wetting and spreading performances of a agricultural chemical liquid, and preventing a drop of the liquid from running down from a subject such as a plant or an insect to increase an amount attached, thereby efficacy-enhancing the agricultural chemical, in the agricultural chemical-spreading agent composition of the present invention, a weigh ratio of the content of the component (A) to the sum of contents of components (B) and (C), (A)/[(B)+(C)], is 10/90 to 40/60, preferably 15/75 to 35/65, and more preferably 20/80 to 35/65.

Conventionally, cellulose derivatives, which are typical polysaccharides, have been often used in granular formulations. In this case, cellulose derivatives used have low viscosity. From the study by the present inventors, in the agricultural chemical-spreading agent composition, cellulose derivatives having low viscosity are found to lack the ability to provide sufficient attachment of an agricultural active ingredient such as an agricultural chemical and a fertilizer used together with the spreading agent composition to a subject such as a plant or an insect. However, cellulose derivatives having high viscosity are found to cause gel formation and/or an increase in viscosity of a single-liquid composition when formulated in the composition at high concentration. The reason why the component (A) having high viscosity can achieve easy preparation, improve storage stability of a composition, and be formulated in the composition at an increased concentration is unknown, but assumed that use of components (A) to (C) at contents within specific rages described above enables to provide a composition delivering well-balanced performances of components (B) and (C) and containing the component (A) at an increased concentration.

For facilitation of preparation, improving storage stability of a composition, thickening the component (A), improving wetting and spreading performances of an agricultural chemical liquid, and preventing a drop of the liquid from running down from a subject such as a plant or an insect to increase an amount attached, thereby efficacy-enhancing the agricultural chemical, in the agricultural chemical-spreading agent composition of the present invention, a weigh ratio of contents of components (B) to (C), (B)/(C), is preferably 60/40 to 25/75, more preferably 55/45 to 25/75, and even more preferably 50/50 to 30/70.

For improving wetting and spreading performances of an agricultural chemical liquid, thickening the component (A), and preventing a drop of the liquid from running down from a subject such as a plant or an insect to increase an amount attached, thereby efficacy-enhancing the agricultural chemical, the agricultural chemical-spreading agent composition of the present invention preferably contains components (B) and (C) in the total amount of 20 to 50% by weight, more preferably 30 to 50% by weight, and even more preferably 25 to 45% by weight.

The agricultural chemical-spreading agent composition of the present invention can further contain a fixing agent such as casein and a dispersing agent such as naphthalenesulfonic acid-formaldehyde condensate and lignin sulfonate.

<Agricultural Chemical Composition>

The agricultural chemical composition of the present invention contains the agricultural chemical-spreading agent composition of the present invention as described above and an agricultural chemical ingredient. As used herein, the "agricultural chemical ingredient" refers to an active ingredient in an agricultural chemical. The agricultural chemical composition of the present invention can contain an agricultural chemical ingredient selected from active ingredients in bactericides, pesticides, miticides, herbicides, and plant growth regulators together with the agricultural chemical-spreading agent composition of the present invention.

For improving wetting and spreading performances of an agricultural chemical liquid and preventing a drop of the liquid from running down from a subject such as a plant or an insect to increase an amount attached, thereby efficacy-enhancing the agricultural chemical, the agricultural chemical composition of the present invention preferably contains the agricultural chemical-spreading agent composition of the present invention in an amount of 1 to 20% by weight, and more preferably 2 to 15% by weight.

The agricultural chemical composition of the present invention can be in any form of preparation, including emulsion, liquid, wettable powder, granule, powder, and flowable concentrate. The agricultural chemical composition thus may contain other additive according to its preparation form, including an emulsifier, a solvent, a dispersant, and a carrier. The agricultural chemical-spreading agent composition according to the present invention can be used by using an agricultural chemical composition in one of the above shown forms containing the agricultural chemical-spreading agent composition. Alternatively it can be used when an agricultural chemical (without the spreading agent composition of the present invention) is diluted in use. In either of these cases, the spreading agent composition of the present invention can achieve intended effects for spreading an agricultural chemical.

The preparation of the agricultural chemical composition of the present invention may further contain a chelating agent, a pH adjusting agent, an inorganic salt, and/or a thickener according to need.

Examples of the chelating agent that can be used in the present invention include aminopolycarboxylic acid chelating agents, aromatic and aliphatic carboxylic acid chelating agents, amino acid chelating agents, ether polycarboxylic acid chelating agents, phosphonic acid chelating agents (e.g., iminodimethylphosphonic acid (IDP) and alkyldiphosphonic acid (ADPA)), dimethylglyoxime (DG), hydroxycarboxylic acid chelating agents, and polyelectrolyte (including oligomer) chelating agents. These agents may be used in a free acid form or a salt form such as of sodium, potassium, and ammonium. The chelating agent is added in an amount of 0.01 to 30 molar times as much as the total amount of components (B) and (C) in the agricultural chemical-spreading agent composition.

Any aminopolycarboxylic acid chelating agent can be used, including:
a) $RNX_2$-type compounds,
b) $NX_3$-type compounds,
c) R—NX—$CH_2CH_2$—NX—R-type compounds,
d) R—NX—$CH_2CH_2$—$NX_2$-type compounds, and
e) $X_2N$—R'—$NX_2$-type compounds,
wherein, X represents —$CH_2COOH$ or —$CH_2CH_2COOH$; R represents a hydrogen atom, an alkyl group, a hydroxy group, a hydroxyalkyl group, or a group representing such a known chelating compound; R' represents an alkylene group, a cycloalkylene group, and a group representing such a known chelating compound. Typical examples of the chelating agent include ethylenediaminetetraacetic acid (EDTA), cyclohexanediaminetetraacetic acid (CDTA), nitrilotriacetic acid (NTA), iminodiacetic acid (IDA), N-(2-hydroxyethyl) iminodiacetic acid (HIMDA), diethylenetriaminepentaacetic acid (DTPA), N-(2-hydroxyethyl)ethylenediaminetriacetic acid (EDTA-OH), and glycol ether diamine tetraacetic acid (GEDTA), and salts thereof.

Examples of the chelating agent that can be used in the present invention include: for aromatic and aliphatic carboxylic acid chelating agents, oxalic acid, succinic acid, pyruvic acid, anthranilic acid, and salts thereof; for amino acid chelating agents, glycine, serine, alanine, lysine, cystine, cysteine, ethionine, tyrosine, and methionine, and salts and derivatives thereof; for hydroxycarboxylic acid chelating agents, glycolic acid, malic acid, citric acid, gluconic acid, heptonic acid, acetic acid, and salts thereof; and for ether polycarboxylic acid chelating agents, compounds represented by the following formula and analogues and salts (particularly Na salt) thereof.

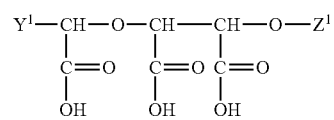

in the formula,
$Y^1 = $ —H, —$CH_2COOH$ or —COOH $Z^1 = $ —H, —$CH_2COOH$ or —CHCOOH
$\phantom{Z^1 = \quad\quad\quad\quad\quad\quad\quad\quad\quad\quad\quad}|$
$\phantom{Z^1 = \quad\quad\quad\quad\quad\quad\quad\quad\quad\quad\quad}CH_2COOH$ Examples of the polyelectrolyte (including oligoelectrolyte) chelating agent that can be used in the present invention include acrylic acid polymers, maleic anhydride polymers, α-hydroxyacrylic acid polymers, itaconic acid polymers, and copolymers thereof, and epoxysuccinic acid polymers.

Examples of the pH adjusting agent that can be used in the present invention include citric acid, phosphoric acid (pyrophosphoric acid), gluconic acid, or salts thereof. Note that, although the agricultural chemical-spreading agent composition of the present invention can have any pH, from the viewpoint of stability of a preparation, the pH of the spreading agent composition is preferably 3 to 9, and more preferably 4 to 8.

Examples of the inorganic salt that can be used in the present invention include inorganic mineral salts such as inorganic clay, talc, bentonite, zeolite, calcium carbonate, diatomite, and white carbon, and inorganic ammonium salts such as ammonium sulfate, ammonium nitrate, ammonium phosphate, ammonium thiocyanate, ammonium chloride, and ammonium sulfamate.

Next, examples of the thickener that can be used in the present invention include synthetic water-soluble thickeners. Specific examples of the synthetic water-soluble thickener include polyacrylates, polymaleates, polyvinylpyrrolidone, and pentaerythritol-ethylene oxide adducts.

Examples of the agricultural chemical ingredient in the agricultural chemical composition of the present invention include, but not limited to, those described in "Nouyaku handobukku 2001 nendoban (Agricultural chemical handbook 2001 edition)" (Japan Plant Protection Association). The agricultural chemical-spreading agent composition of the present invention has no harmful effects on various products and can be used safely.

Examples of the bactericide include sulfur-based zineb (zinc ethylenebisdithiocarbamate) and maneb (manganese ethylenebisdithiocarbamate); benzimidazole-based benomyl (methyl-1-(butylcarbamoyl)-2-benzimidazole carbamate); dicarboximide-based vinclozolin (3-(3,5-dichlorophenyl)-5-methyl-5-vinyl-1,3-oxazolidine-2,4-dione), iprodione (3-(3,5-dichlorophenyl)-N-isopropyl-2,4-dioxoimidazolidine-1-carboxamide), and procymidone (N-(3,5-dichlorophenyl)-1,2-dimethylcyclopropane-1,2-dicarboximide); and others such as triazine (2,4-dichloro-6-(2-chloroanilino)-1,3,5-triazine), triflumizole ((E)-4-chloro-α,α,α-trifluoro-N-(1-imidazole-1-yl-2-propoxyethylidene)-o-toluidine), metalaxyl (methyl-N-(2-methoxyacetyl)-N-(2,6-xylyl)-D,L-alaninate), organocopper compounds (e.g., oxine-copper), cupric hydroxide (e.g., Kocide Bordeaux mixture), and antibiotic bactericides (streptomycins, tetracyclins, polyoxy-type bactericides, Blasticidin S, kasugamycins, and validamycins). Among these bactericides, preferred are organocopper compounds (e.g., Oxine-copper), cupric hydroxide, triflumizole ((E)-4-chloro-α,α,α-trifluoro-N-(1-imidazole-1-yl-2-propoxyethylidene)-o-toluidine), iprodione (3-(3,5-dichlorophenyl)-N-isopropyl-2,4-dioxoimidazolidine-1-carboxamide).

Examples of the pesticide include: pyrethroid pesticides such as permethrin ((3-phenoxybenzyl (1RS,3RS)-(1RS, 3RS)-3-(2,2-dichlorovinyl)-2,2-dimethylcyclo propane carboxylate); organophosphorus pesticides such as CYAP (O,O-dimethyl-O-p-cyanophenyl thiophosphate), Sumithion (MEP) (O,O-dimethyl-O-(3-methyl-4-nitrophenyl) thiophosphate), and DDVP (dimethyl 2,2-dichlorovinylphosphate); and carbamate pesticides such as Bassa (O-sec-butylphenyl methylcarbamate), methomyl (S-methyl N-[(methylcarbamoyl)oxy]thioacetimide), and cartap (1,3-bis(carbamoylthio)-2-(N,N-dimethylamino)propane hydrochloride). Among these pesticides, preferred are permethrin, DDVP (dimethyl 2,2-dichlorovinylphosphate), and methomyl (S-methyl N-[(methylcarbamoyl)oxy]thioacetimide).

Examples of the natural pesticide include pyrethrin and piperonyl butoxide compositions of pyrethrum origin, and rotenone and nicotinic (3-(1-methyl-2-pyrrolidinyl)pyridine sulfate) compositions of derris origin, which is a leguminous plant. Examples of an insect growth regulator (IGR agent) include diflubenzuron (1-(4-chlorophenyl)-3-(2,6-difluorobenzoyl)urea).

Examples of the miticide include CPCBS (p-chlorophenyl p-chlorobenzenesulfonate), phenisobromolate (4,4'-dibromobenzilic acid isopropyl ester), hexythiazox (trans-5-(4-chlorophenyl)-N-cyclohexyl-4-methyl-2-oxothiazo lidine-3-carboxamide), tetradifon (2,4,5,4'-tetrachlorodiphenylsulfone), fenothiocarb (S-4-phenoxybutyl dimethylthiocarbamate), fenpyroximate (tert-butyl (E)-α-(1,3-dimethyl-5-phenoxypyrazol-4-ylmethyleneaminooxy-p-toluate), and amitraz(3-methyl-1,5-bis(2,4-xylyl)-1,3,5-triazapenta-1,4-diene). Among these miticides, preferred are phenisobromolate (4,4'-dibromobenzilic acid isopropyl ester), hexythiazox (trans-5-(4-chlorophenyl)-N-cyclohexyl-4-methyl-2-oxothiazo lidine-3-carboxamide), amitraz(3-methyl-1,5-bis(2,4-xylyl)-1,3,5-triazapenta-1,4-diene), and fenpyroximate (tert-butyl (E)-α-(1,3-dimethyl-5-phenoxypyrazol-4-ylmethyleneaminooxy)-p-toluate).

Examples of the herbicide include: acid amide herbicides such as Stam (3,4-dichloropropionanilide, DCPA); urea herbicides such as DCMU (3-(3,4-dichlorophenyl)-1,1-dimethylurea) and linuron (3-(3,4-dichlorophenyl)-1-methoxy-1-methylurea); dipyridyl herbicides such as paraquat (1,1'-dimethyl-4,4'-bipyridinium dichloride) and diquat (6,7-dihydrodipyrido[1,2-a:2',1' c]pyrazinediium dibromide); diazine herbicides such as bromacil (5-bromo-3-sec-butyl-6-methyluracil); S-triazine herbicides such as simazine (2-chloro-4,6-bis(ethylamino)-1,3,5-triazine) and simetryn (2,4-bis(ethylamino)-6-methylthio-1,3,5-triazine); nitrile herbicides such as DBN (2,6-dichlorobenzonitrile); dinitroaniline herbicides such as trifluralin (α,α,α-trifluoro-2,6-dinitro-N,N-dipropyl-p-toluidine); carbamate herbicides such as benthiocarb (Saturn) (S-p-chlorobenzyl-N,N-diethylthiocarbamate) and MCC (methyl-3,4-dichlorocarbanilate); diphenyl ether herbicides such as NIP (2,4-dichlorophenyl p-nitrophenyl ether); phenol herbicides such as PCP (sodium pentachlorophenoxide); benzoic acid herbicides such as MDBA (dimethylamine 3,6-dichloro-o-anisate); phenoxy herbicides such as 2,4-D sodium salt (sodium 2,4-dichlorophenoxyacetate) and Mapica ([(4-chloro-o-toluoyl)oxy]acet-o-chloroaniline); amino acid herbicides such as glyphosate (N-(phosphonomethyl)glycine or a salt thereof), Bialaphos (sodium salt of L-2-amino-4-[(hydroxy) (methyl)=phosphinoyl]butyryl-L-alanyl-L-alanine), and glufosinate (ammonium-DL-homoalanine-4-yl(methyl)-phosphinate); and aliphatic herbicides such as TCA-sodium (sodium trichloroacetate). Among these herbicides, preferred are DBN (2,6-dichlorobenzonitrile), DCMU (3-(3,4-dichlorophenyl)-1,1-dimethylurea), paraquat (1,1'-dimethyl-4,4'-bipyridinium dichloride), and diquat (6,7-dihydrodipyrido[1,2-a:2',1'c]pyrazinediium dibromide).

The agricultural chemical composition of the present invention can further contain one or more other plant growth regulators, fertilizers, and/or preservatives than those described above in combination.

Examples of the plant growth regulator include indolebutyric acid, ethychlozate (ethyl 5-chloro-3-(1H)indazolylacetate), benzylaminopurine (6-(N-benzylamino)purine), forchlorfenuron (1-(2-chloro-4-pyridyl)-3-phenylurea), gibberellin, decyl alcohol, and ethephon (2-chloroethylphosphonic acid).

In the present invention, for bactericidal, pesticidal, miticidal, or herbicidal purpose or purpose of control of plant growth, used is the agricultural chemical composition containing an agricultural chemical ingredient and the agricultural chemical-spreading agent composition of the present invention in an amount of 0.03 to 50 times, preferably 0.1 to 50 times, and more preferably 0.3 to 35 times the amount of the agricultural chemical ingredient.

The agricultural chemical preparation containing the agricultural chemical-spreading agent composition of the present invention may be one including an individual package of the efficacy-enhancing agent composition of the present invention and an package of an agricultural chemical component. It may be one including an individual package of the agricultural chemical-spreading agent composition for of the present invention, an individual package of the other surfactant(s) than the components (A), (B), and (C), and an individual package of an agricultural chemical composition. The agricultural chemical component of the individual package contains an agricultural chemical ingredient and any optional ingredient at any ratio, in the form of emulsion, a wettable powder or the like. Each individual package can be of any form and adequately prepared according to an intended use and purpose.

Further, according to the present invention, also provided is a method for producing an agricultural product, containing a step of applying the agricultural chemical-spreading agent composition of the present invention and an agricultural chemical ingredient selected from active ingredients in bactericides, pesticides, miticides, herbicides and plant growth regulators to a subject sensitive to the agricultural chemical ingredient, or containing a step of applying the agricultural chemical composition of the present invention to a subject sensitive to the agricultural chemical ingredient. The subject can be treated with the agricultural chemical-spreading agent composition, the agricultural chemical ingredient, or the agricultural chemical composition in any way, including the above-described direct spraying of a composition containing an agricultural chemical and the agricultural chemical-spreading agent composition on a leaf, a stem, or a fruit or the like, and addition of a diluted agricultural chemical composition to a mineral nutrient solution or supplied water contacting with a root in hydroponics or cultivation in rock wool to supply (apply) to the surface of the root or the like. To effectively achieve effects of the agricultural chemical-spreading agent composition of the present invention (effects to enhance attachment of an active ingredient to a subject such as a plant), application of the spreading agent composition to a subject sensitive to an agricultural chemical ingredient is preferably conducted by spraying the efficacy-enhancer composition on an aerial part of a subject, and more preferably on a leaf. The agricultural chemical-spreading agent composition of the present invention and an agricultural chemical ingredient may also be separately applied to a subject sensitive to the agricultural chemical ingredient by the method as described above.

In the method for producing an agricultural product of the present invention, the agricultural chemical-spreading agent composition of the present invention is used together with an agricultural chemical ingredient in the situation of using an agricultural chemical. The subject of the method of the present invention includes bactericides against bacteria, pesticides against pests (insects), miticides against mites, herbicides against weeds (not falling under the category of an agricultural product), and plant growth regulators for an agricultural product (plant to be cultivated). The method can be applied to a single subject or plural subjects. The method can be performed as targeting to a subject selected from plants, pests, and bacteria, (for example, by spreading the agricultural chemical composition in a cultivating land of agricultural products. In this case, plants include agricultural products and/or weeds.

In these methods of the present invention, examples of the agricultural product as the subject of the efficacy-enhancer composition of the present invention and an agricultural chemical ingredient, or the agricultural chemical composition (containing the efficacy-enhancer composition of the present invention and an agricultural chemical ingredient) include fruit vegetables such as cucumber, pumpkin, watermelon, melon, tomato, eggplant, green pepper, strawberry, okra, green bean, broad bean, pea, edamame bean, and corn; leaf vegetables such as napa cabbage, brassica vegetables, baby bok choy, cabbage, cauliflower, broccoli, Brussels sprout, onion, leek, garlic, Chinese onion, garlic chives, asparagus, lettuce, butterhead lettuce, celery, spinach, garland chrysanthemum, parsley, Japanese honewort, Japanese parsley, Japanese spikenard, myoga ginger, giant butterbur, and shiso; and root vegetables such as daikon, turnip, edible burdock, carrot, potato, eddoe, sweet potato, yam, ginger, lotus; andothers such as rice, Triticeae crops, and flowers and ornamental plants.

Examples of the weed include Bermuda glass (*Cynodon dactylon*), Egyptian crowfoot grass (*Dactyloctenium aegyptium*), jungle rice (*Echinochloa colona*), cockspur grass (*Echinochloa crus-galli*), Indian goosegrass (*Eleusine indica*), southern crabgrass (*Digitaria ciliaris*), blady grass (*Imperata cylindrica*), southern cut grass (*Leersia hexandra*), Chinese sprangletop (*Leptochloa chinensis*), torpedograss (*Panicum repens*), Napier grass (*Pennisetum purpureum*), itchgrass (*Rottboellia exaltata*), cattail grass (*Setaria pumila* ssp. *pallidefusca*), variable flatsedge (*Cyperus difformis*), rice flatsedge (*Cyperus iria*), purple nutsedge (*Cyperus rotundus*), umbrella sedge (*Fuirena ciliaris*), Indian jointvetch (*Aeschynomene indica*), flossflower (*Ageratum houstonianum*), sessile joyweed (*Alternanthera sessilis*), redroot amaranth (*Amaranthus retroflexus*), Benghal dayflower (*Commelina benghalensis*), creeping spiderwort (*Commelina diffusa*. Burm, f.), common water hyacinth (*Eichhornia crassipes*), asthma weed (*Euphorbia pilulifera*), Indian heliotrope (*Heliotropium indicum*), chan (*Hyptis suaveolens*), nardoo (*Marsilea crenata* C.Presl), sensitive plant (*Mimosa pudica*), oval-leafed pondweed (*Monochoria vaginalis* var. *plantaginea*), verdolaga (*Portulaca oleracea*), coat buttons (*Tridax procumbens*), velvetleaf (*Abutilon theophrasti*), and field horsetail (*Equisetum arvense*).

Further, the agricultural chemical-spreading agent composition of the present invention can also efficacy-enhance an agricultural chemical. Therefore, the present invention further provides a method for efficacy-enhancing an agricultural chemical, containing applying an agricultural chemical ingredient selected from bactericides, pesticides, miticides, herbicides, and plant growth regulators together with the agricultural chemical-spreading agent composition of the present invention to a subject sensitive to the agricultural chemical ingredient.

EXAMPLES

The following Examples demonstrate the present invention. Examples are intended to illustrate the present invention, and not to limit the present invention.

Example 1 and Comparative Example 1

Tables 1 to 3 show components (A) to (C) and Comparative components used in the following Examples and Comparative Examples. Note that, a 5% viscosity of a polysaccharide was measured by the following method.

[5% Viscosity]

In accordance with the method of measuring a viscosity, the second method of the Pharmacopeia of Japan, 14th edition, part 1, measurement using a rotational viscometer, a 5% viscosity was measured as follows. First, to 95 mL of water at 25° C. was added 5.000 g of dried polysaccharides with stirring. The mixture was stirred for 10 minutes with a stirrer, heated to 85° C., further mixed for additional 1 hour, and put in an ice-water bath and stirred to dissolve the polysaccharides, and added with water to make an amount 100.0 g. The mixture was centrifuged to separate from foams to obtain a measurement sample. Next, in a B-type viscometer (Toki Sangyo Co., Ltd., model: TVB-10, rotor: No. 23), set up such that the axis of rotation of the viscometer was perpendicular to the horizontal plane, the measurement sample (100.0 g) was put and allowed to stand for 1 hour in a thermostat bath at 25° C. The apparatus was then operated (rotation number of rotor: 4 rpm). After the rotation reached to a steady state and an indicator scale for rotation number or torque of the viscometer shown a stable value, the value was read and used to calculate a viscosity. In cases of viscosities over 100000 mPa·s as measured with a B-type viscometer, a helical viscometer (Toki Sangyo Co., Ltd., model: VHS-1, rotor: No. T-D, rotation number of rotor: 2.5 rpm was used instead of the B-type viscometer to determine a viscosity.

Spreading agent compositions shown in Tables 4 to 6 were prepared with components in Tables 1 to 3 and 4 to 6, and evaluated for (1) easiness in preparation and (2) storage stability by the following methods. Results are shown in Tables 4 to 6. In some of Comparative compositions, a comparative component corresponding to a component (A) or (C) was considered as a component (A) or (C) and used to determine respective weight proportions.

(1) Easiness in Preparation

A spreading agent composition immediately after prepared were visually observed and ranked according to the following scale.

A: A composition was easily prepared without generating a gel.

B: A composition was prepared, but generated a gel.

C: A composition could not be prepared due to an increased viscosity.

(2) Storage Stability (Test of Stability at 40° C.)

A spreading agent composition was put in a glass bottle, and stored for 10 days at 40° C. For evaluation, the stored composition was allowed to stand for 1 hour at a room temperature (25° C.), visually observed, compared with a control sample of a composition stored for 10 days at 25° C., and ranked according to the following scale.

A: No sedimentation or no separation.

B: some separation, but becoming homogeneous by stirring.

C: Separation and some sedimentation, but becoming homogeneous by stirring.

D: Sedimentation and separation, not becoming homogeneous by stirring.

TABLE 1

| | Symbol | Name of compound | Trade name | Manufacturer | 5% viscosity (mPa · s) |
|---|---|---|---|---|---|
| Component (A) | Polysaccharide 1 | Guar gum | Meypro-Guar CSA-200-50 | Sansho Co., Ltd | 616000 |
| | Polysaccharide 2 | Hydroxypropyl guar gum | Meypro HPG8111 | Sansho Co., Ltd | 776000 |
| | Polysaccharide 3 | carboxy methyl hydroxy propyl guar gum | JAGUARC-8600 | Sansho Co., Ltd | 3160000 |
| | Polysaccharide 4 | Carboxymethylated starch | Kiprogum M-800A | Nippon starch chemical Co., Ltd | 14000 |
| | Polysaccharide 5 | Hydroxyalkylated starch | Piostarch H | Nippon starch chemical Co., Ltd | 21000 |
| | Polysaccharide 6 | Hydroxypropyl cellulose | HPC-H | Nippon Soda Co., Ltd | 50000 |
| | Polysaccharide 7 | Hydroxypropyl methylcellulose | Metlose 90SH-30000 | Shin-Etsu Chemical Co., Ltd | 476000 |
| | Polysaccharide 8 | Starch acetate | Z-300F | Nippon starch chemical Co., Ltd | 9000 |
| Comparative polysaccharide | Polysaccharide 9 | Carboxymethyl cellulose | CMC 1105 | Daicel Corporation | 70 |
| | Polysaccharide 10 | Starch | Soluble starch | Wako Pure Chemical Industries, Ltd | 757 |

TABLE 2

| | Symbol | Name of compound |
|---|---|---|
| Component (B) | Surfactant B1 | Polyoxyethylene(20) sorbitane oleic acid ester |

TABLE 2-continued

| Symbol | Name of compound |
|---|---|
| SurfactantB2 | Polyoxyethylene(20) sorbitane lauric acid ester |
| Surfactant B3 | Polyoxyethylene(20) sorbitane palmitic acid ester |

The number in parentheses represents an average mole number of oxyethylene groups added (the same applies hereinafter).

TABLE 3

| | Symbol | Name of compound |
|---|---|---|
| Component (C) | Surfactant C1 | Sorbitan oleate ester |
| | Surfactant C2 | Sorbitan laurate ester |
| | Surfactant C3 | Sorbitan palmitate ester |
| | Surfactant C4 | Polyoxyethylene(4) lauryl ether |
| | Surfactant C5 | Polyoxyethylene(5) lauryl ether |
| | Surfactant C6 | Polyoxyethylene(6) lauryl ether |
| | Surfactant C7 | Polyoxyethylene(12) stearyl ether |
| | Surfactant C8 | Polyoxyalkylene-modified heptamethyltrisiloxane* |
| Comparative surfactant | Surfactant C9 | Sodium laurate |

*Polyoxyalkylene-modified heptamethyltrisiloxane: Silwet L-77 (Momentive Performance Materials Inc.,)

TABLE 4

| | | | | Product of the invention | | | | | | | | | | | |
|---|---|---|---|---|---|---|---|---|---|---|---|---|---|---|---|
| | | | | 1 | 2 | 3 | 4 | 5 | 6 | 7 | 8 | 9 | 10 | 11 | 12 |
| Agricultural chemical-spreading agent composition | Composition (% by weight) | (A) | Polysaccharide 1 | 10.0 | 10.0 | 10.0 | 10.0 | 10.0 | 10.0 | 10.0 | 20.0 | | | | |
| | | | Polysaccharide2 | | | | | | | | | 5.0 | | | |
| | | | Polysaccharide3 | | | | | | | | | | 10.0 | | |
| | | | Polysaccharide4 | | | | | | | | | | | 10.0 | |
| | | | Polysaccharide5 | | | | | | | | | | | | 10.0 |
| | | | Polysaccharide6 | | | | | | | | | | | | |
| | | | Polysaccharide7 | | | | | | | | | | | | |
| | | | Polysaccharide 8 | | | | | | | | | | | | |
| | | | Polysaccharide 9 | | | | | | | | | | | | |
| | | | Polysaccharide 10 | | | | | | | | | | | | |
| | | (B) | Surfactant B1 | 11.0 | 20.0 | 20.0 | 20.0 | 20.0 | 20.0 | 25.0 | 13.5 | | 20.0 | | 20.0 |
| | | | Surfactant B2 | | | | | | | | | 20.0 | | | |
| | | | Surfactant B3 | | | | | | | | | | | 16.0 | |
| | | (C) | Surfactant C1 | 14.0 | 25.0 | 25.0 | 25.0 | 25.0 | 25.0 | 20.0 | | | | | 25.0 |
| | | | Surfactant C2 | | | | | | | | 31.5 | | | | |
| | | | Surfactant C3 | | | | | | | | | 25.0 | | | |
| | | | Surfactant C4 | | | | | | | | | | | 29.0 | |
| | | | Surfactant C5 | | | | | | | | | | 25.0 | | |
| | | | Surfactant C6 | | | | | | | | | | | | |
| | | | Surfactant C7 | | | | | | | | | | | | |
| | | | Surfactant C8 | | | | | | | | | | | | |
| | | (D) | Diethylene glycol | 20.0 | 20.0 | | | | | 24.0 | 20.0 | 20.0 | 20.0 | 20.0 | 20.0 |
| | | | Propylene glycol | | | 20.0 | | | | | | | | | |
| | | | Dipropylene glycol | | | | 20.0 | | | | | | | | |
| | | | Diethylene glycol monomethyl ether | | | | | 25.0 | | | | | | | |
| | | | Butyl cellusolve | | | | | | 25.0 | | | | | | |
| | | | Purified water | 45.0 | 25.0 | 25.0 | 25.0 | 20.0 | 20.0 | 21.0 | 15.0 | 30.0 | 25.0 | 25.0 | 25.0 |
| | | | (A)/[(B) + (C)] (weight ratio) | 29/71 | 18/82 | 18/82 | 18/82 | 18/82 | 18/82 | 18/82 | 18/82 | 31/69 | 10/90 | 18/82 | 18/82 |
| | | | (B)/(C) (weight ratio) | 44/56 | 44/56 | 44/56 | 44/56 | 44/56 | 44/56 | 56/44 | 30/70 | 44/56 | 44/56 | 36/64 | 44/56 |
| Easiness in preparation | | | | B | A | A | A | A | A | B | A | B | A | A | A |
| Storage stability | | | | A | A | A | A | A | A | A | A | A | A | A | B |

TABLE 5

| | | | | Product of the invention | | | | | | | | | |
|---|---|---|---|---|---|---|---|---|---|---|---|---|---|
| | | | | 13 | 14 | 15 | 16 | 17 | 18 | 19 | 20 | 21 | 22 |
| Agricultural spreading agent composition | Composition (% by weight) | (A) | Polysaccharide 1 | 10.0 | 10.0 | 10.0 | 8.0 | 10.0 | 10.0 | 10.0 | 11.0 | 20.0 | 5.0 |
| | | | Polysaccharide 2 | | | | 2.0 | | | | 1.0 | | |
| | | | Polysaccharide 3 | | | | | | | | | | |
| | | | Polysaccharide 4 | | | | | | | | | | |
| | | | Polysaccharide 5 | | | | | | | | | | |
| | | | Polysaccharide 6 | | | | | | | | | | |
| | | | Polysaccharide 7 | | | | | | | | | | |
| | | | Polysaccharide8 | | | | | | | | | | |
| | | | Polysaccharide 9 | | | | | | | | | | |
| | | | Polysaccharide 10 | | | | | | | | | | |
| | | (B) | Surfactant B1 | 20.0 | 20.0 | 20.0 | 20.0 | 20.0 | 15.0 | 13.5 | 20.0 | 13.5 | 20.0 |
| | | | Surfactant B2 | | | | | | | | | | |
| | | | Surfactant B3 | | | | | | | | | | |

TABLE 5-continued

|  |  |  |  |  |  |  |  |  |  |  |  |
|---|---|---|---|---|---|---|---|---|---|---|---|
|  |  | (C) Surfactant C1 |  |  |  | 25.0 |  |  | 31.5 | 25.0 | 31.5 | 25.0 |
|  |  | Surfactant C2 |  |  |  |  | 25.0 | 25.0 |  |  |  |  |
|  |  | Surfactant C3 |  |  |  |  |  |  |  |  |  |  |
|  |  | Surfactant C4 |  |  |  |  |  |  |  |  |  |  |
|  |  | Surfactant C5 |  |  |  |  |  |  |  |  |  |  |
|  |  | Surfactant C6 | 25.0 |  |  |  |  |  |  |  |  |  |
|  |  | Surfactant C7 |  | 25.0 |  |  |  |  |  |  |  |  |
|  |  | Surfactant C8 |  |  | 25.0 |  |  |  |  |  |  |  |
|  | (D) | Diethylene glycol | 20.0 | 20.0 | 20.0 | 20.0 |  |  |  | 20.0 | 20.0 | 20.0 |
|  |  | Propylene glycol |  |  |  |  | 25.0 | 25.0 | 10.0 |  |  |  |
|  |  | Dipropylene glycol |  |  |  |  |  |  |  |  |  |  |
|  |  | Diethylene glycol monomethyl ether |  |  |  |  |  |  |  |  |  |  |
|  |  | Butyl cellusolve |  |  |  |  |  |  |  |  |  |  |
|  |  | Purified water | 25.0 | 25.0 | 25.0 | 25.0 | 20.0 | 25.0 | 35.0 | 23.0 | 15.0 | 30.0 |
|  |  | (A)/[(B) + (C)] (weight ratio) | 18/82 | 18/82 | 18/82 | 18/82 | 18/82 | 20/82 | 18/82 | 21/79 | 31/69 | 10/90 |
|  |  | (B)/(C) (weight ratio) | 44/56 | 44/56 | 44/56 | 44/56 | 44/56 | 38/63 | 30/70 | 44/56 | 30/70 | 44/56 |
| Easiness in preparation |  |  | A | A | A | A | A | A | A | A | A | B |
| Storage stability |  |  | A | A | A | A | A | A | B | A | A | A |

|  |  |  |  | Product of the invention ||||||||
|---|---|---|---|---|---|---|---|---|---|---|---|
|  |  |  |  | 23 | 24 | 25 | 26 | 27 | 28 | 29 | 30 |
| Agricultural spreading agent composition | Composition (% by weight) | (A) | Polysaccharide 1 | 10.0 | 10.0 | 10.0 | 10.0 | 10.0 |  |  |  |
|  |  |  | Polysaccharide 2 |  |  |  |  |  |  |  |  |
|  |  |  | Polysaccharide 3 |  |  |  |  |  |  |  |  |
|  |  |  | Polysaccharide 4 |  |  |  |  |  |  |  |  |
|  |  |  | Polysaccharide 5 |  |  |  |  |  |  |  |  |
|  |  |  | Polysaccharide 6 |  |  |  |  |  | 10.0 |  |  |
|  |  |  | Polysaccharide 7 |  |  |  |  |  |  | 10.0 |  |
|  |  |  | Polysaccharide 8 |  |  |  |  |  |  |  | 5.0 |
|  |  |  | Polysaccharide 9 |  |  |  |  |  |  |  |  |
|  |  |  | Polysaccharide 10 |  |  |  |  |  |  |  |  |
|  |  | (B) | Surfactant B1 | 29.0 | 9.0 | 6.6 | 20.0 | 20.0 | 20.0 | 20.0 | 20.0 |
|  |  |  | Surfactant B2 |  |  |  |  |  |  |  |  |
|  |  |  | Surfactant B3 |  |  |  |  |  |  |  |  |
|  |  | (C) | Surfactant C1 | 16.0 | 36.0 | 8.4 | 25.0 | 25.0 | 25.0 | 25.0 | 25.0 |
|  |  |  | Surfactant C2 |  |  |  |  |  |  |  |  |
|  |  |  | Surfactant C3 |  |  |  |  |  |  |  |  |
|  |  |  | Surfactant C4 |  |  |  |  |  |  |  |  |
|  |  |  | Surfactant C5 |  |  |  |  |  |  |  |  |
|  |  |  | Surfactant C6 |  |  |  |  |  |  |  |  |
|  |  |  | Surfactant C7 |  |  |  |  |  |  |  |  |
|  |  |  | Surfactant C8 |  |  |  |  |  |  |  |  |
|  |  | (D) | Diethylene glycol | 20.0 | 20.0 | 20.0 | 45.0 |  | 20.0 | 20.0 |  |
|  |  |  | Propylene glycol |  |  |  |  |  |  |  | 20.0 |
|  |  |  | Dipropylene glycol |  |  |  |  |  |  |  |  |
|  |  |  | Diethylene glycol monomethyl ether |  |  |  |  |  |  |  |  |
|  |  |  | Butyl cellusolve |  |  |  |  |  |  |  |  |
|  |  |  | Purified water | 25.0 | 25.0 | 55.0 | 0.0 | 45.0 | 25.0 | 25.0 | 30.0 |
|  |  |  | (A)/[(B) + (C)] (weight ratio) | 18/82 | 18/82 | 40/60 | 18/82 | 18/82 | 18/82 | 18/82 | 10/90 |
|  |  |  | (B)/(C) (weight ratio) | 64/36 | 20/80 | 44/56 | 44/56 | 44/56 | 44/56 | 44/56 | 44/56 |
| Easiness in preparation |  |  |  | B | B | B | B | B | A | A | B |
| Storage stability |  |  |  | B | B | B | B | C | A | A | A |

TABLE 6

|  |  |  |  | Comparative product ||||||||
|---|---|---|---|---|---|---|---|---|---|---|---|
|  |  |  |  | 1 | 2 | 3 | 4 | 5 | 6 | 7 | 8 |
| Agricultural chemical-spreading agent composition | Composition (% by weight) | (A) | Polysaccharide 1 | 10.0 | 10.0 | 10.0 | 10.0 | 3.0 | 34.0 | 10.0 | 10.0 |
|  |  |  | Polysaccharide 2 |  |  |  |  |  |  |  |  |
|  |  |  | Polysaccharide 3 |  |  |  |  |  |  |  |  |
|  |  |  | Polysaccharide 4 |  |  |  |  |  |  |  |  |
|  |  |  | Polysaccharide 5 |  |  |  |  |  |  |  |  |
|  |  |  | Polysaccharide 6 |  |  |  |  |  |  |  |  |
|  |  |  | Polysaccharide 7 |  |  |  |  |  |  |  |  |
|  |  |  | Polysaccharide 8 |  |  |  |  |  |  |  |  |
|  |  |  | Polysaccharide 9 |  |  |  |  |  |  |  |  |
|  |  |  | Polysaccharide 10 |  |  |  |  |  |  |  |  |
|  |  | (B) | Surfactant B1 |  | 20.0 |  |  | 7.0 | 22.0 | 20.0 |  |
|  |  |  | Surfactant B2 |  |  |  |  |  |  |  |  |
|  |  |  | Surfactant B3 |  |  |  |  |  |  |  |  |

TABLE 6-continued

| | | | | | | | | | |
|---|---|---|---|---|---|---|---|---|---|
| (C) Surfactant C1 | | | | 25.0 | | 20.0 | 28.0 | | 40.0 |
| Surfactant C2 | | | | | | | | | |
| Surfactant C3 | | | | | | | | | |
| Surfactant C4 | | | | | | | | | |
| SurfactantC5 | | | | | | | | | |
| SurfactantC6 | | | | | | | | | |
| SurfactantC7 | | | | | | | | | |
| SurfactantC8 | | | | | | | | | |
| SurfactantC9 | | | | | | | | | |
| (D) Diethylene glycol | | | | | 20.0 | 20.0 | 10.0 | 20.0 | 20.0 |
| Propylene glycol | | | | | | | | | |
| Dipropylene glycol | | | | | | | | | |
| Diethylene glycol monomethyl ether | | | | | | | | | |
| Butyl cellosolve | | | | | | | | | |
| Purified water | | | 90.0 | 70.0 | 65.0 | 70.0 | 50.0 | 6.0 | 50.0 | 30.0 |
| (A)/[(B) + (C)] (weight ratio) | | | 100/0 | 33/67 | 29/71 | 100/0 | 10/90 | 40/60 | 33/67 | 20/80 |
| (B)/(C) (weight ratio) | | | — | 100/0 | 0/100 | — | 26/74 | 44/56 | 100/0 | 0/100 |
| Easiness in preparation | | | C | C | A | A | C | C | A | A |
| Storage stability | | | — | — | D | D | — | — | D | D |

| | | | | Comparative product | | | | | |
|---|---|---|---|---|---|---|---|---|---|
| | | | | 9 | 10 | 11 | 12 | 13 | 14 |
| Agricultural chemical-spreading agent composition | Composition (% by weight) | (A) | Polysaccharide 1 | 10.0 | 10.0 | | | 30.0 | 5.0 |
| | | | Polysaccharide 2 | | | | | | |
| | | | Polysaccharide 3 | | | | | | |
| | | | Polysaccharide 4 | | | | | | |
| | | | Polysaccharide 5 | | | | | | |
| | | | Polysaccharide 6 | | | | | | |
| | | | Polysaccharide 7 | | | | | | |
| | | | Polysaccharide 8 | | | | | | |
| | | | Polysaccharide 9 | | | 10.0 | | | |
| | | | Polysaccharide 10 | | | | 10.0 | | |
| | | (B) | Surfactant B1 | 20.0 | 20.0 | 20.0 | 20.0 | 15.0 | 25.0 |
| | | | Surfactant B2 | | | | | | |
| | | | Surfactant B3 | | | | | | |
| | | (C) | Surfactant C1 | | | 25.0 | 25.0 | 20.0 | 30.0 |
| | | | Surfactant C2 | | | | | | |
| | | | Surfactant C3 | | | | | | |
| | | | Surfactant C4 | | | | | | |
| | | | SurfactantC5 | | | | | | |
| | | | SurfactantC6 | | | | | | |
| | | | SurfactantC7 | | | | | | |
| | | | SurfactantC8 | | | | | | |
| | | | SurfactantC9 | 25.0 | 25.0 | | | | |
| | | (D) | Diethylene glycol | | 20.0 | 20.0 | 20.0 | 20.0 | 20.0 |
| | | | Propylene glycol | | | | | | |
| | | | Dipropylene glycol | | | | | | |
| | | | Diethylene glycol monomethyl ether | | | | | | |
| | | | Butyl cellosolve | | | | | | |
| | | | Purified water | 45.0 | 25.0 | 25.0 | 25.0 | 15.0 | 20.0 |
| | (A)/[(B) + (C)] (weight ratio) | | | 18/82 | 18/82 | 18/82 | 18/82 | 46/54 | 8/92 |
| | (B)/(C) (weight ratio) | | | 44/56 | 44/56 | 44/56 | 44/56 | 43/57 | 45/55 |
| Easiness in preparation | | | | C | B | A | A | C | C |
| Storage stability | | | | — | D | D | D | — | — |

Example 2 and Comparative Example 2

Spreading agent compositions in Example 1 and Comparative Example 1 were subjected to a herbicidal test, an insecticidal test, a miticidal test, and a bactericidal test according to the following methods. Results are shown in Table 7. Note that, although some of compositions in Comparative Example 1 were difficult to be prepared, these were forced to form a spreading agent composition by vigorous agitation or the like, and used in the following test.

[Herbicidal Test]

Plants of Cockspur grass were cultivated in 12 cm pots. Individuals having about 18 cm height were used to conduct the test. Each agricultural chemical composition was prepared by mixing 1 L of water with 4.8 g of Roundup liquid (herbicide available from Nissan Chemical Industries, Ltd., effective ingredient: 41% by weight glyphosate in the form isopropylamine salt) and 2.0 g of spreading agent composition shown in Tables 4 to 6. An agricultural chemical composition was applied in an amount shown in Table 7 over the plant by foliar spraying, and evaluated for a herbicidal activity. For evaluation, 14 days after from spraying, an aerial part of the plant was weighed and used to calculate a herbicidal rate according to the following equation, based on a weight of a fresh aerial part of a plant in an untreated area (without being sprayed with an agricultural chemical itself). The higher herbicidal rate refers to the higher agricultural chemical activity (herbicidal activity). In the test, the "untreated area" refers to an area in which an agricultural chemical composition containing an agricultural chemical and a spreading agent composition was not sprayed (the same applied to other tests).

herbicidal rate (%)=[(weight of an aerial part in an untreated area)−(weight of an aerial part in a treated area)]/(weight of an aerial part in an untreated area)×100

From results shown in Table 7, agricultural chemical compositions of the present invention were confirmed to enhance the herbicidal effect.

[Insecticidal Test]

Plants of rice were cultivated in 12 cm pots to a height of 15 cm. 10 imagoes of Unka (an insect member of the order Homoptera) 3 to 5 days old from emergence were released per plant of rice three times and allowed to grow. Each agricultural chemical composition was prepared by mixing 1 L of water with 0.3 g of Sumithion emulsion (pesticide available from Sumitomo Chemical Co., Ltd., effective ingredient; 50% by weight fenitrothion) and 2.0 g of spreading agent composition shown in Tables 4 to 6. An agricultural chemical composition was applied in an amount shown in Table 7 over the plant of rice infested with Unka by foliar spraying. Plants were dried in the air and covered with a woven metal cylinder for 3 days. Then, the number of survival insects was counted and used to calculate an insecticidal rate according to the following equation. The higher insecticidal rate refers to the higher agricultural chemical activity (insecticidal activity).

insecticidal rate (%)=[(the number of survival insects in an untreated area)−(the number of survival insects in a treated area)]/(the number of survival insects in an untreated area)×100

From results shown in Table 7, agricultural chemical compositions of the present invention were confirmed to enhance the insecticidal activity.

[Miticidal Test]

Plants of kidney bean were cultivated in 12 cm pots to a stage of five leaves. 30 individuals of *Tetranychus kanzawai* were released per plant three times. Each agricultural chemical composition was prepared by mixing 1 L of water with 0.3 g of Nissorun wettable powder (miticide available from Nippon Soda Co., Ltd., effective ingredient: 10% by weight hexythiazox) and 2.0 g of spreading agent composition shown in Tables 4 to 6. An agricultural chemical composition was applied in an amount shown in Table 7 over the plant of kidney bean by foliar spraying. Plants were dried in the air and covered with a woven metal cylinder for 3 days. Then, the number of survival mites was counted and used to calculate a miticidal rate according to the following equation. The higher miticidal rate refers to the higher agricultural chemical activity (miticidal activity).

miticidal rate (%)=[(the number of survival mites in an untreated area)−(the number of survival mites in a treated area)]/(the number of survival mites in an untreated area)×100

From results shown in Table 7, agricultural chemical compositions of the present invention were confirmed to enhance the miticidal activity.

[Bactericidal Test]

Plants of cucumber were cultivated in 12 cm pots to a stage of three leaves. To these plants, a suspension of spores (at a concentration of $10^7$ spores/mL) of cucumber gray mold-causing fungus (*Botrytis cinerea*) resistant to bactericides was sprayed at a rate of 50 mL/10a. Plants were allowed to stand at 25° C. under 90% relative humidity to be infected by the fungi. Three days after from the infection, each agricultural chemical composition was prepared by mixing 1 L of water with 0.5 g of Benlate wettable powder (bactericide available from Sumitomo Chemical Co., Ltd., effective ingredient: 50% by weight benomyl) and 2.0 g of spreading agent composition shown in Tables 4 to 6. An agricultural chemical composition was applied in an amount shown in Table 7 over the plant of cucumber by foliar spraying. Pots were allowed to stand at 25° C. under 85% relative humidity for a week. Then, the number of lesions was counted and used to calculate a controlling value according to the following equation. The higher controlling value refers to the higher agricultural chemical activity (bactericidal activity).

controlling value (%)={1−(the number of lesions in a treated area/the number of lesions in an untreated area)}×100

From results shown in Table 7, agricultural chemical compositions of the present invention were confirmed to enhance the bactericidal activity.

TABLE 7

|  |  | A agricultural chemical-spreading agent composition | Sprayed amount of agricultural chemical composition | Herbicidal rate (%) | Insecticidal test (%) | Miticidal rate (%) | Controlling value |
|---|---|---|---|---|---|---|---|
| Example | 2-1 | Inventive product 1 | 100L/10a | 81 | 79 | 81 | 78 |
|  | 2-2 | Inventive product 2 | 100L/10a | 86 | 84 | 86 | 82 |
|  | 2-3 | Inventive product 3 | 100L/10a | 88 | 85 | 89 | 86 |
|  | 2-4 | Inventive product 4 | 100L/10a | 90 | 89 | 91 | 88 |
|  | 2-5 | Inventive product 5 | 100L/10a | 92 | 90 | 93 | 90 |
|  | 2-6 | Inventive product 6 | 100L/10a | 84 | 81 | 84 | 80 |
|  | 2-7 | Inventive product 7 | 100L/10a | 90 | 87 | 91 | 88 |
|  | 2-8 | Inventive product 8 | 100L/10a | 94 | 92 | 94 | 91 |
|  | 2-9 | Inventive product 9 | 100L/10a | 78 | 76 | 79 | 76 |
|  | 2-10 | Inventive product 10 | 100L/10a | 79 | 77 | 80 | 78 |
|  | 2-11 | Inventive product 11 | 100L/10a | 76 | 74 | 77 | 73 |
|  | 2-12 | Inventive product 12 | 100L/10a | 91 | 86 | 90 | 87 |
|  | 2-13 | Inventive product 13 | 100L/10a | 91 | 86 | 90 | 87 |
|  | 2-14 | Inventive product 14 | 100L/10a | 84 | 82 | 85 | 82 |
|  | 2-15 | Inventive product 15 | 100L/10a | 78 | 74 | 77 | 73 |
|  | 2-16 | Inventive product 16 | 100L/10a | 93 | 92 | 94 | 91 |
|  | 2-17 | Inventive product 17 | 100L/10a | 90 | 87 | 90 | 86 |
|  | 2-18 | Inventive product 18 | 100L/10a | 86 | 83 | 85 | 82 |
|  | 2-19 | Inventive product 19 | 100L/10a | 83 | 80 | 84 | 81 |
|  | 2-20 | Inventive product 20 | 100L/10a | 96 | 93 | 96 | 93 |
|  | 2-21 | Inventive product 23 | 100L/10a | 76 | 79 | 80 | 78 |

TABLE 7-continued

|  |  | A agricultural chemical-spreading agent composition | Sprayed amount of agricultural chemical composition | Herbicidal rate (%) | Insecticidal test (%) | Miticidal rate (%) | Controlling value |
|---|---|---|---|---|---|---|---|
|  | 2-22 | Inventive product 24 | 100L/10a | 78 | 78 | 79 | 76 |
|  | 2-23 | Inventive product 25 | 100L/10a | 75 | 77 | 77 | 72 |
|  | 2-24 | Inventive product 26 | 100L/10a | 85 | 84 | 86 | 83 |
|  | 2-25 | Inventive product 27 | 100L/10a | 72 | 68 | 71 | 66 |
|  | 2-26 | Inventive product 28 | 100L/10a | 91 | 89 | 92 | 89 |
|  | 2-27 | Inventive product 29 | 100L/10a | 89 | 88 | 91 | 87 |
|  | 2-28 | Inventive product 1 | 7L/10a | 75 | 73 | 76 | 72 |
|  | 2-29 | Inventive product 2 | 7L/10a | 76 | 73 | 76 | 72 |
|  | 2-30 | Inventive product 7 | 7L/10a | 82 | 80 | 83 | 80 |
|  | 2-31 | Inventive product 8 | 7L/10a | 90 | 85 | 88 | 83 |
|  | 2-32 | Inventive product 21 | 7L/10a | 74 | 72 | 76 | 71 |
|  | 2-33 | Inventive product 22 | 7L/10a | 76 | 73 | 74 | 71 |
|  | 2-34 | Inventive product 30 | 100L/10a | 80 | 77 | 79 | 77 |
| Comparative example | 2-1 | Comparative composition 1 | 100L/10a | 47 | 43 | 48 | 44 |
|  | 2-2 | Comparative composition 2 | 100L/10a | 61 | 56 | 61 | 55 |
|  | 2-3 | Comparative composition 3 | 100L/10a | 55 | 50 | 54 | 51 |
|  | 2-4 | Comparative composition 4 | 100L/10a | 50 | 47 | 52 | 48 |
|  | 2-5 | Comparative composition 5 | 100L/10a | 59 | 56 | 60 | 57 |
|  | 2-6 | Comparative composition 6 | 100L/10a | 66 | 64 | 66 | 63 |
|  | 2-7 | Comparative composition 7 | 100L/10a | 66 | 63 | 65 | 64 |
|  | 2-8 | Comparative composition 8 | 100L/10a | 60 | 56 | 60 | 57 |
|  | 2-9 | Comparative composition 9 | 100L/10a | 62 | 58 | 61 | 56 |
|  | 2-10 | Comparative composition 10 | 100L/10a | 63 | 58 | 62 | 55 |
|  | 2-11 | Comparative composition 11 | 100L/10a | 57 | 56 | 59 | 55 |
|  | 2-12 | Comparative composition 12 | 100L/10a | 55 | 56 | 60 | 57 |
|  | 2-13 | Comparative composition 13 | 100L/10a | 51 | 48 | 53 | 48 |
|  | 2-14 | Comparative composition 14 | 100L/10a | 58 | 55 | 59 | 57 |

The invention claimed is:

1. An agricultural chemical-spreading agent composition, comprising: (A) a polysaccharide in an amount of 5 to 30% by weight; (B) a polyoxyalkylene sorbitan fatty acid ester in an amount of 5 to 30% by weight; and (C) at least one nonionic surfactant selected from the group consisting of polyoxyalkylene alkyl ethers, sorbitan fatty acid esters, and silicone surfactants in an amount of 5 to 40% by weight, wherein the component (A) has a viscosity of not less than 5000 mPa·s in the form of a 5% by weight aqueous solution at 25° C., and a weight ratio of contents of the component (A) to the sum of components (B) and (C), (A)/[(B)+(C)], is 10/90 to 40/60, and wherein the component (A) is at least one polysaccharide selected from the group consisting of guar gum and derivatives thereof, starch and derivatives thereof, cellulose, hydroxyethyl cellulose, hydroxypropyl cellulose, and hydroxypropylmethyl cellulose.

2. The agricultural chemical-spreading agent composition according to claim 1, wherein a weight ratio of components (B) to (C), (B)/(C), is 60/40 to 25/75.

3. The agricultural chemical-spreading agent composition according to claim 1, further comprising (D) at least one organic solvent selected from the group consisting of polyhydric alcohols and glycol ethers.

4. The agricultural chemical-spreading agent composition according to claim 3, wherein component (D) is at least one organic solvent selected from the group consisting of ethylene glycol, diethylene glycol, propylene glycol, diethylene glycol monomethyl ether and butyl cellosolve.

5. The agricultural chemical-spreading agent composition according to claim 3, which contains component (D) in the amount of 5 to 30% by weight.

6. The agricultural chemical-spreading agent composition according to claim 1, wherein a viscosity of the component (A) in the form of a 5% by weight aqueous solution at 25° C. is 5000 to 3500000 mPa·s.

7. An agricultural chemical composition, comprising the agricultural chemical-spreading agent composition according to claim 1 and an agricultural chemical ingredient selected from the group consisting of active ingredients in bactericides, pesticides, miticides, herbicides, and plant growth regulators.

8. The agricultural chemical composition according to claim 7, which contains the agricultural chemical-spreading agent composition in the amount of 1 to 20% by weight based on the total weight of the agricultural chemical composition.

9. A method for producing an agricultural product, comprising a step of applying the agricultural chemical-spreading agent composition according to claim 1 and an agricultural chemical ingredient selected from the group consisting of active ingredients in bactericides, pesticides, miticides, herbicides, and plant growth regulators to a subject sensitive to the agricultural chemical ingredient.

10. A method for producing an agricultural product, comprising a step of applying the agricultural chemical composition according to claim 7 to a subject sensitive to the agricultural chemical ingredient.

11. A method for efficacy-enhancing an agricultural chemical, comprising applying an agricultural chemical ingredient selected from the group consisting of active ingredients in bactericides, pesticides, miticides, herbicides, and plant growth regulators together with the agricultural chemical-spreading agent composition according to claim 1 to a subject sensitive to the agricultural chemical ingredient.

12. The agricultural chemical-spreading agent composition according to claim 1, wherein the total amount of components (B) and (C) is 20 to 50% by weight.

13. The agricultural chemical-spreading agent composition according to claim 1, wherein component (B) is selected from the group consisting of polyoxyethylene sorbitan oleic acid esters, polyoxyethylene sorbitan lauric acid esters and polyoxyethylene sorbitan palmitic acid esters.

14. The agricultural chemical-spreading agent composition according to claim 1, wherein component (C) is sorbitan fatty acid ester.

* * * * *